US 6,689,302 B2

(12) United States Patent
Reisdorf et al.

(10) Patent No.: US 6,689,302 B2
(45) Date of Patent: Feb. 10, 2004

(54) METHOD OF MAKING AN ANTIMICROBIAL TYMPANOSTOMY TUBE

(75) Inventors: Dennis J. Reisdorf, Jacksonville, FL (US); James B. Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 22 days.

(21) Appl. No.: 10/106,930

(22) Filed: Mar. 26, 2002

(65) Prior Publication Data

US 2002/0147441 A1 Oct. 10, 2002

Related U.S. Application Data

(62) Division of application No. 09/291,151, filed on Apr. 12, 1999, now Pat. No. 6,361,526, which is a continuation of application No. 08/146,300, filed on Nov. 1, 1993, now abandoned.

(51) Int. Cl.[7] .............................................. B29C 45/16
(52) U.S. Cl. ..................... 264/325; 264/299; 264/349
(58) Field of Search .................. 264/325, 299, 264/349, 328.4; 425/201

(56) References Cited

U.S. PATENT DOCUMENTS

| 3,807,409 A | 4/1974 | Paparella et al. |
| 3,916,873 A | 11/1975 | Wasserman |
| 3,976,081 A | 8/1976 | Lapidot |
| 4,054,139 A | 10/1977 | Crossley |
| 4,094,303 A | 6/1978 | Johnston |
| 4,479,795 A | 10/1984 | Mustacich et al. |
| 4,592,920 A | 6/1986 | Murtfeldt |
| 4,603,152 A | 7/1986 | Laurin et al. |
| 4,615,705 A | 10/1986 | Scales et al. |
| 4,650,488 A | 3/1987 | Bays et al. |
| 4,677,143 A | 6/1987 | Laurin et al. |
| 4,695,275 A | 9/1987 | Bruce et al. |
| 4,704,126 A | 11/1987 | Baswell et al. |
| 4,744,792 A | 5/1988 | Sander et al. |
| 4,908,381 A | 3/1990 | Greenwald et al. |
| 4,917,685 A | 4/1990 | Bayston et al. |
| 5,026,378 A | 6/1991 | Goldsmith, III |
| 5,049,140 A | 9/1991 | Brenner et al. |
| 5,165,952 A | 11/1992 | Solomon et al. |
| 5,198,171 A * | 3/1993 | Kasahara et al. ...... 264/211.23 |
| 5,254,120 A | 10/1993 | Cinberg et al. |
| 5,292,516 A | 3/1994 | Viegas et al. |
| 5,350,580 A | 9/1994 | Muchow et al. |
| 5,468,811 A | 11/1995 | Moro et al. |
| 5,645,787 A * | 7/1997 | Taruno et al. ......... 264/272.17 |
| 5,741,224 A | 4/1998 | Milder et al. |
| 5,753,269 A | 5/1998 | Groh et al. |
| 5,820,608 A | 10/1998 | Luzio et al. |
| 5,945,115 A | 8/1999 | Dunn et al. |
| 6,268,405 B1 | 7/2001 | Yao et al. |

* cited by examiner

Primary Examiner—Michael Colaianni
Assistant Examiner—Monica A Fontaine

(57) ABSTRACT

An antimicrobial tympanostomy tube used to alleviate bacteriostatic infections following myringotomy which is compatible with otologic tissue associated with the middle ear. The tube is formed from a microporous thermoplastic or thermoset resin having incorporated therein 0.5 to about 15% by weight of a silver compound capable of migrating to the surface of tube sidewalls to impart a therapeutically effective level of antibacterial activity throughout the sidewall surface so as to provide long-term prevention of infections which may otherwise result during or after surgery or implantation of the tube.

20 Claims, No Drawings

METHOD OF MAKING AN ANTIMICROBIAL TYMPANOSTOMY TUBE

This is a divisional application of U.S. patent application Ser. No. 09/291,151 filed Apr. 12, 1999, and now U.S. Pat. No. 6,361,526B1. which is a continuation of U.S. patent application Ser. No. 08/146,300 filed Nov. 1, 1993 and now abandoned.

BACKGROUND OF THE INVENTION

1. Field of the Invention

The present invention relates to a tympanostomy tube and more particularly to an antimicrobial tympanostomy tube designed to reduce the occurrence of post-operative otorrhea following myringotomy frequently encountered with the insertion of such tubes in the ear.

2. Description of the Prior Art

The use of tympanostomy tubes for the treatment of otitis media with effusion is the most commonly performed surgical procedure in the United States. Children with persistent middle ear effusions who do not respond to antibiotics undergo a procedure in which a myringotomy is performed in the tympanic membrane under general anesthesia.

In this procedure an incision is made in the tympanic membrane, fluid from within the middle ear is aspirated and a tympanostomy tube is inserted. The tubes can have various configurations and materials, and are effective in correcting the hearing loss due to the effusion as long as the tubes are in place in the ear. The materials which can be used to make tympanostomy tubes include thermoplastics such as modified elastomers and olefins, thermosets such as silicone and polytetrafluoroethylene; and metals such as stainless steel and titanium.

Purulent otorrhea frequently develops after tube insertion. In one study by H. G. Birck and J. J. Mravek "Myringotomy for Middle Ear Effusions," Ann. of Otol. Rhino. Laryngo., volume 85, pages 263–267 (1979), the investigators observed that 15% of children having tympanostomy tubes inserted in their ears following myringotomy developed postoperative otorrhea. In a more recent study by George A. Gates et al, "Post Tympanostomy Otorrhea," Laryngoscope, volume 96, pages 630–634, (June 1986), the investigators observed that the incidence of tympanostomy tube induced otorrhea following myringotomy was 18%. In a clinical study performed by Balkany et al, "A Prospective Study of Infection Following Tympanostomy and Tube Insertion," American Journal of Otology, volume 4, pages 288–291 (1983), the investigators observed an incidence of postoperative otorrhea of 19% in children receiving tympanostomy tubes with no antibiotic drops postoperatively applied. In the Balkany et al study, the investigators found that the incidence of postoperative otorrhea was reduced to 6% when antibiotic drops were put into the patient's ear after myringotomy. In another study on the use of antibiotics after myringotomy, R. S. Baker and R. A. Chole, "A Randomized Clinical Trial of Topical Gentamicia After Tympanostomy Tube Placement," Arch. Otolaryngology Head and Neck Surgery, volume 114, pages, 755–757 (July 1988), the investigators found that the incidence of infections in the experimental group using Gentamicin, an ophthalmic solution used as otic drops, had an incidence of infection significantly reduced by antibiotic drops.

In both the Balkany et al and Baker et al studies using antibiotic drops after tympanostomy, the investigators used potentially ototoxic antibiotics, namely Cortisporin and Gentamicin. Based on their frequency of use, and the lack of adverse effects noted in these studies, antibiotic drops are now used routinely to prevent postoperative otorrhea. However, thorough studies demonstrating the absence of adverse toxicological reaction in the use of antibiotic drugs for the treatment of postoperative otorrhea have not been published.

In addition to the relatively high incidence of otorrhea after myringotomy, investigators have observed children with implanted tympanostomy tubes sometimes experience bouts of otorrhea. Occasionally, the otorrhea became persistent causing some investigators to believe that the tympanostomy tubes become colonized with pathogenic bacteria.

The relatively high incidence of otorrhea after myringotomy and tympanostomy tube insertion exposes patients with persistent middle ear effusions to significant morbidity and additional treatment time and cost.

It would be desirable to utilize tympanostomy tubes whereby the incidence of otorrhea and other microbial induced infection after myringotomy and tympanostomy tube insertion could be substantially reduced without the use of antibiotics and the potential ototoxic reaction associated with the use of such drugs.

One approach for reducing bacterial infection encountered with the use of medical devices inserted into body cavities has been to apply an antimicrobial coating to the surface of the medical device. For example, U.S. Pat. No. 4,592,920 to Murtfeldt; U.S. Pat. No. 4,603,152 to Laurin et al and U.S. Pat. No. 4,677,143 to Laurin et al each teach applying a coating containing an antimicrobial agent such as silver oxide to the outer surfaces of medical devices such as catheters, enteral feeding tubes, endotracheal tubes and other hollow tubular devices.

U.S. Pat. No. 4,592,920 to Murtfeldt is primarily concerned with providing a surface coating of an antimicrobial metal compound on a medical device such as a catheter, but also discloses that the metal compound can be "imbedded" within the entire catheter. However, the Murtfeldt patent finds the imbedded construction to be less desirable since the antimicrobial metal compound imbedded within the side wall of the catheter has less likelihood of encountering migrating microbes and by inference is less effective than a surface coating.

SUMMARY OF THE INVENTION

In accordance with the present invention, it has been found that tympanostomy tubes formed from a microporous, highly flexible thermoplastic or thermoset resin having a high gas permeability rate and having about 0.5 to 15% by weight of a silver compound incorporated throughout the sidewall of the tympanostomy tube exhibits sufficient antimicrobial activity to alleviate or prevent postoperative bacterial infections normally associated with the use of these tubes and without adverse toxicological reaction with otologic tissue such as irritation or inflammation.

DESCRIPTION OF THE PREFERRED EMBODIMENTS

The tympanostomy tube of the present invention is characterized by its biological compatibility with otologic tissue associated with the middle ear and contains silver additives, such as silver oxide incorporated therein which are capable of migrating ions or other formed compounds to the surface of the tube sidewall to impart a therapeutically effective amount of antimicrobial activity to the sidewall surface.

Moreover, the release of antimicrobial agents from the tube sidewalls proceeds at a rate adapted to provide long term prophylaxis for the prevention of post-operative otorrhea following myringotomy with the insertion of tympanostomy tubes, thereby reducing the need for the prophylactic administration of antibiotics.

Dispersing the silver oxide throughout the tube instead of using a surface coating is preferred for a number of reasons, including:

1. There is significant difficulty associated with coating a product the size of an ear ventilation tube. Tube geometries typically are cylindrical in shape with abrupt diameter changes and odd shaped flanges. The tube geometry and small tube size make it difficult to control coating thickness. Dispersing the metal oxide homogeneously throughout the tube assures an even distribution of the metal oxide throughout the tube including the inner lumen area.
2. It is also believed that the metal oxide will be functional over a longer period of time when dispersed throughout the tube, rather than as a coated product since a tube material such as silicone with its high permeability rates will provide pathways for the oxide to migrate to the surface and provide antimicrobial activity for a period of time longer than a surface coating.
3. It is easier to control the amount of the silver oxide present in the tube when it exists as a homogeneous dispersion throughout the tube, compared with a silver oxide coating on the surface of the tube. This is because a change in tube thickness varies the oxide contact and the thickness of the coating is difficult to control.

The antimicrobial tympanostomy tube of the present invention can be prepared by mixing a suitable microporous elastomeric resin having a relatively high gas permeability rate, for example about $26 \times 10^{-9}$ cubic centimeters ($cm^3$) of air through one square centimeter ($cm^2$), surface area membrane 1 centimeter thick in 1 second at 1 centimeter of Hg pressure, with a concentration of silver additives or compounds ranging from about 0.5 to about 15% by weight of the resin.

To insure thorough and uniform dispersion of the silver containing additive or compound in the resin, the resin is preferably in the form of a paste and the silver compound in the form of particles having an average particle size of about 5 to about 100 microns, which are milled thoroughly to facilitate uniform dispersion of the silver compound in the resin paste.

The milled product is then formed into a hollow tube by any conventional tube forming process such as transfer molding, extrusion or casting. Once formed, the tube is cured to its final form by baking the tube in the mold or in an oven at a temperature sufficient for curing the resin paste. The product is packaged and sterilized before shipment, as for example with ethylene oxide in a manner which is well known to those skilled in the art.

Resins which are microporous and have the requisite high gas permeability properties can be used to prepare the antimicrobial tympanostomy tubes of the present invention. These resins are characterized by an ability to transmit or leach antimicrobial silver ions. The resins include curable silicones, PVA'S, thermoplastic elastomers, acrylonitrile-butadiene-styrene copolymer rubber, and polyurethanes. Curable silicone resins are preferred for the manufacture of the antimicrobial tympostomy tubes of the present invention due to their molecular structure which provides good flexibility both microscopically and macroscopically, and high gas permeability rates.

TABLE 1

Gas Permeability (cc/.001 inch/100 sq. in./24 hr. @ Atm 73° F., 0% relative humidity, ASTM D-1434)[1]

| | $O_2$ | $CO_2$ |
|---|---|---|
| Silicone | 50,000 | 300,000 |
| Urethanes | 200 | 3,000 |
| Epoxies | 5–10 | 8 |
| Fluorocarbons | 7–15 | 15–30 |
| Nylon | 2.6 | 4.7 |
| Polybutylene | 385 | 825 |
| Polycarbonate | 258 | 775 |
| Cellulose Acetate | 23 | 105 |

[1]Packaging Encyclopedia 1988 Vol. 33 No. 5, pages 54–55, Machine Design May 25, 1967, page 192

Silver compounds which provide the antimicrobial silver ions and which can be incorporated in the sidewall of the antimicrobial tympanostomy tube of the present invention include silver oxide, silver chloride, silver iodide, silver acetate, silver citrate, silver nitrate, silver sulfadiazine, and silver sulfate, with silver oxide being preferred.

In the examples which follow, all parts and percentages are by weight unless otherwise indicated.

EXAMPLE 1

An antimicrobial tympanostomy tubing having a sidewall thickness of 0.2 millimeters (mm) and an inner diameter of 0.9–1.25 mm containing varying concentrations of silver as silver oxide ($Ag_2O$) dispersed throughout the tube sidewalls was prepared by mixing purified silver oxide with paste silicone available from the Dow Chemical Company under the designation Dow Silicone MDX4-4515 Paste Silicone. Other equivalent silicone gum resins from various suppliers can also be used. The silicone paste and a purified silver oxide powder having a 5–50 micron diameter particle size were blended together and milled thoroughly to insure full and complete dispersion of the silver oxide throughout the silicone. The silver oxide concentrations were about 5, 9 and 13% by weight. The milled product was transfer molded into a common tympanostomy tube shape and post cured at 120° C. for 1.5 hours. The cured product was then tumble deflashed, washed with deionized water, Liquinox (Alconox, Inc.) and alcohol. The washed product was then sterilized with ethylene oxide in a 12/88 cycle at 60° C. for 6½ hour exposure before testing.

The antimicrobial activity of the silver modified tympanostomy tubes was demonstrated through in-vitro testing utilizing the following antimicrobial assay protocol. The microorganisms used in the assay were:

| Microorganism | No. |
|---|---|
| C. albicans | 1 |
| A. niger | 2 |
| E. coli | 3 |
| P. aeruginosa | 4 |
| S. aureus | 5 |
| C. xerosis | 6 |
| S. epidermidis | 7 |

The inoculum preparation was carried out by first inoculating soybean-casein digest agar medium plates with a recently grown stock culture of each of the above-identified microorganisms. The bacterial cultures were grown at 35°±2° C. for 18–24 hours. The culture of C. albicans was grown at 20°–25° C. for 48 hours and the *A. niger* culture was grown at 20°–25° C. for 1 week.

All the cultures except *A. niger* were harvested using sterile USP saline to wash the surface growth into sterile glass vessels equipped with screw top lids. The *A. niger* culture was harvested in the same manner except sterile USP saline containing 0.05% Tween 80 (Atlas Chemical Ind.), was used as the wash solution.

The colony forming units per milliliter (titers) were determined for each culture using a standard plate count method. USP purified water was used for the titering. The plate count served to determine how much of the stock solution was needed to seed the test plates and if dilution was necessary before seeding.

Testing was performed in triplicate for each sample. Mueller-Hinton agar (MHA) was used as the test media. The MHA plates were seeded with enough culture inoculum to permit vigorous confluent growth. Sections of 1.7 mm diameter×5 mm long of the silver modified silicone tympanostomy tubing having varying concentrations of silver dispersed throughout the sidewall were aseptically transferred to the inoculated media surfaces. All the assays except the *C. albicans* and *A. niger* assays were incubated at 35° C.±2° C. for 18 to 24 hours. The *C. albicans* assay was incubated for 24 to 48 hours at 20° to 25° C. The *A. niger* assay was incubated for 1 week, or until a clear zone delineation was recognized at 20° to 25° C.

The diameter of the zones of inhibition that formed around the tubes was measured from the approximate midpoint of the tube to the zone edge. The zones were measured to the nearest tenth of a millimeter.

The assay results are recorded in Table 2. Each result recorded in Table 2 is the zone of inhibition in millimeters (mm) and is the average of the 3 samples tested for each microbial organism tested.

TABLE 2

| Tube | Concentration of $Ag_2O$ in tube (wt.%) | Zones of Inhibition (mm.) Test Microorganisms | | | | | | |
|---|---|---|---|---|---|---|---|---|
| | | 1 | 2 | 3 | 4 | 5 | 6 | 7 |
| I | 5.74 | 4.8 | 8.6 | 2.4 | 3.1 | 2.5 | 3.0 | 8.97 |
| II | 8.97 | 5.0 | 8.9 | 4.7 | 3.1 | 3.4 | 5.0 | 4.9 |
| III | 12.67 | 3.9 | 6.1 | 4.8 | 3.6 | 3.2 | 3.2 | 5.1 |

The data recorded in Table 2 indicates that all samples exhibited zonal properties for each microorganism assayed at silver oxide concentrations of about 5.7%, 9.0% and 12.7%, and that zone sites did not tend to materially increase with concentration.

EXAMPLE 2

For comparative purposes, the procedure of Example 1 was repeated with a control using tubing which did not contain any silver. This tubing did not exhibit any zonal inhibition, and microbial growth appeared right up to the edge of the tubing surface for each microorganism assayed.

EXAMPLE 3

In addition to the bacteriostatic testing described above, the silver oxide modified silicone was evaluated for its effect on a live animal ear. Silicone wafers were prepared having varying concentrations of silver oxide, specifically 1%, 5% and 20% by weight silver oxide in silicone. In addition, 100% $Ag_2O$ powder in 1 $mm^3$ and 7 $mm^3$ amounts was prepared. The silicone wafers and silver oxide powder were tested for otologic tissue compatibility. All samples were placed on the round window membrane in the ear of guinea pigs. The results from the tests indicated that no significant irritation or inflammation was caused by any of the samples except for the 100% silver oxide powder which caused hair cell losses and adhesions.

These compatibility test results, demonstrate that tympanostomy tubes incorporating silver oxide concentrations in accordance with the present invention appear to be therapeutically effective for antimicrobial activity without irritation, inflammation or other harmful effects to the middle ear tissue of animals.

EXAMPLE 4

The antimicrobial tympanostomy tubes of the present invention were also evaluated for hemolysis, cytotoxicity and implant sensitivity. Hemolysis testing of cured silicone resin having dispersed therein 5.7, 9.0 and 12.7% by weight concentrations of silver oxide was performed in the following manner:

Extraction Method: A 6.0 gram portion of the test material was placed in 30 ml of 0.9% sodium chloride solution and extracted at 50° C. for 72 hours. The extract was divided into two tubes of 10 ml each and allowed to cool to room temperature.

To each extract and similarly treated control tube was added 0.2 ml of rabbit blood previously collected in a vacuum tube containing E.D.T.A. The tubes were inverted gently to mix the contents, then placed in a constant temperature water bath at 37° C. for 1 hour. The blood-saline mixture, positive and negative controls were then centrifuged for 10 minutes at a speed of not less than 2100 revolutions per minute (rpm).

The absorbance of each sample solution was determined spectrophotometrically at 545 nm. Similarly, absorbances were recorded for the positive control (10 ml water and 0.2 ml blood) and the negative control (10 ml 0.9% sodium chloride solution and 0.2 ml blood). The blood-saline mixture, positive and negative controls were recentrifuged for 5 minutes at a speed of not less than 2100 rpm to ensure a constant absorbance reading had been obtained.

Cytotoxicity of the silver oxide modified silicone wafers was determined in the following manner:

A monolayer of L-929 Mouse Fibroblast cells was grown to confluency and exposed to an extract of the test sample prepared by placing the sample material in 20 ml of Minimum Essential Medium (Eagle) and bovine serum (5%) and extracting at 37° C. for 24 hours. An MEM aliquot was used as a negative control. After exposure to the extract, the cells were examined microscopically for cytotoxic effect (CTE). Presence (+) or absence (−) of a confluent monolayer, intracellular granulation, cellular swelling and crenation and the percentage of cellular lysis were recorded.

Implant tests in rabbits were performed for 7 and 30 day periods. The procedure was as follows:

Two healthy (minimum) adult New Zealand white rabbits weighing not less than 2.5 Kg. were used as test animals. The rabbits were housed individually and allowed food and water ad libitum. Prior to the implantation the back of each animal was clipped on both sides of the spinal column. All loose hair was removed after clipping and prior to implantation to prevent entry into the implantation site.

Four strips (minimum) of sterilized (by sponsor) test material approximately 1 mm wide and 10 mm long were introduced into the right paravertebral muscle of each rabbit. Two strips of U.S.P. negative control plastic were implanted in the left paravertebral muscle of each rabbit.

The animals were humanely killed 7 or 30 days after implantation and the entire paravertebral muscle on each side of the spinal cord removed. Cross sections of the muscles were made to locate the implants. The tissue surrounding the center portion of each implant was examined macroscopically and microscopically.

The tissues to be examined microscopically were preserved in 10% Neutral Buffered Formalin, sectioned and stained with Hematoxylin and Eosin.

| Scoring Key | |
| --- | --- |
| Score | Capsule Formation |
| 0 | None Noted |
| 1 | Up to 0.5 mm |
| 2 | 0.6 to 1.0 mm |
| 3 | 1.1 to 2.0 mm |
| 4 | >2.0 mm |

| Reaction Index $\bar{X}$ (Test) − $\bar{X}$ (Control) = | |
| --- | --- |
| 0–0.5 | Not Significant |
| 0.6–1.0 | Trace |
| 1.1–2.0 | Slight |
| 2.1–3.0 | Moderate |
| >3.1 | Marked |

The results of this testing were as follows:

TABLE 3

| | Silver oxide ($Ag_2O$) Concentration | | |
| --- | --- | --- | --- |
| | 5.7% | 9.0% | 12.7% |
| Hemolysis[1]: | 5.7% | 6% | 16% |
| Cytotoxicity: | Toxic | Toxic | Toxic |
| 7 day implant: | | | |
| Micro: | Slight irritant | Slight irritant | slight irritant |
| Macro: | Non irritant | Trace irritant | Non irritant |
| 30 day implant: | | | |
| Micro: | Slight irritant | Slight irritant | Non irritant |
| Macro: | Slight irritant | Slight irritant | Slight irritant |

[1]5% or more is considered hemolyltic

The cytotoxicity test performed for Table 3 was based on an agarose overlay and used sample strips of 1 square centimeter in accordance with the following procedure:

A monolayer of L-929 Mouse Fibroblast cells was grown to confluency and overlaid with Minimum Essential Medium supplemented with serum, antibiotics, neutral red, and agarose. The test article was placed on the solidified overlay surface. Following incubation for 24 hours, the culture was macroscopically examined for evidence of cell decolorization to determine the zone of cell lysis. Any decolorized zone present was examined microscopically to confirm cell lysis. The determination of toxicity or nontoxicity was made on the following basis:

| Evaluation | Observations |
| --- | --- |
| Nontoxic: | No change in cell morphology in proximity to test sample. |
| Toxic: | Death and/or degeneration of cells directly beneath the area of test sample and possibly also within a zone extended beyond the test sample. Where a zone of lysis was observed, the distance from the edge of the sample to the edge of the zone was measured and reported in millimeters. |

EXAMPLE 5

For additional comparison, the procedure of Example 1 was repeated with the exception that a silver compound was not incorporated in the sidewalls of the silicone tube. Instead, the tube sidewalls were coated with silver oxide following the procedure of U.S. Pat. No. 4,592,920 to Murtfeldt by suspending the tube in a liquid emulsion of a silicone resin containing silver oxide. The coated tube was cured to form a solid adherent film of the silver oxide modified resin on the surface of the tube.

Tissue toxicity and sensitivity tests performed with these silver coated tubes following the procedure of Example 1 indicated the following results:

(a) Agarose overlay test method for cytotoxicity—Toxic
(b) 7 day implant Micro: Slight irritant Macro: Non irritant
(c) 30 day implant Micro: Slight irritant Macro: Non irritant

EXAMPLE 6

The longevity of antimicrobial activity of the material was tested by the following method:

A. Preparation of Organism Suspension

Using a bacteriological loop, a loopful of S. aureus cells were transferred from the NAmSA stock culture library (TSA slant) to a sterile tube containing 10 ml of 0.85% saline. The tube was vortexed to suspend the cells in the saline. This suspension was used to prepare the organism lawns for each interval and on the day of preparation.

B. Preparation of Organism Challenge Plates

A TSA plate was placed on the pedestal of the rotary plater and allowed to rotate freely. Two sterile swabs were saturated with an organism suspension of S. aureus containing between $10^5$ and $10^6$ colony forming units (CFU). The swabs were pulled outward from the center across the agar surface of the TSA plate to insure the entire surface was inoculated. A separate inoculated TSA plate was prepared for each tympanostomy tube for each of the specified sampling time intervals.

C. Preparation of Controls

The outer packaging of tympanostomy tube cases was opened. Using alcohol flamed forceps, each tympanostomy tube was aseptically transferred directly to separate, inoculated TSA plates by placing the tympanostomy tube passageway perpendicular to the agar surface. The plates were incubated at 30–35° C. for 48 hours. These controls were tested to establish baseline antimicrobial activity present on the tympanostomy tube.

D. Preparation of Test Samples

The outer packaging of each tympanostomy tube case was opened. Using alcohol flamed forceps, each tympanostomy tube was aseptically transferred to a sterile 13×100 mm test tube with a screw cap closure. This procedure was repeated for ten tympanostomy tubes. This portion of the study was performed to evaluate the residual antimicrobial activity of the tympanostomy tubes after extraction with an aqueous solution.

E. Test Procedure 0.3 ml of sterile 0.85% saline was added to each of the test tubes that contained a tympanostomy tube. Two tympanostomy tubes were immediately sampled by aseptically removing the tympanostomy tube with a pair of alcohol flamed forceps and transferring each tympanostomy tube to a separate inoculated TSA plate with the tympanostomy tube passageway perpendicular to the agar surface. The plates were incubated at 30–35° C. for 16 hours. The remaining eight tympanostomy tubes which contained the saline and the tympanostomy tube were placed in a 37° C. incubator for sampling. The inoculated TSA plates were prepared immediately before each of the sampling intervals using the procedure of Step B. Two tympanostomy tubes, held at 37° C. were sampled at weekly intervals for four consecutive weeks following the procedure of Step E.

The results of the longevity study are listed in Table 4 as follows:

TABLE 4

| | Zone of Inhibition (mm) | |
|---|---|---|
| Sampling Interval | TSA Plate 1 | TSA Plate 2 |
| Control | 1 | 2 |
| 0 Day | 1 | <1* |
| 7 Day | 1 | 1 |
| 14 Days | 1 | 1 |
| 21 Days | 1 | 1 |
| 28 Days | 1 | 1 |

*A small zone was present, but it was below the limitations of an accurate measurement.

The bacteriostatic activity of the tympanostomy tubes did not decrease in the article as supplied or following extraction in an aqueous solution for 28 days.

EXAMPLE 7

A double-blind randomized multi-center clinical trial was conducted to compare the incidence of post-operative otorrhea associated with the surgical implantation of the inventive anti-microbial tympanostomy tube and with a control tympanostomy tube in the ears of children with persistent otitis media with effusion or recurrent acute otitis media.

All children in the trial had persistent bilateral otitis media with effusion or recurrent acute otitis media and failed a course of antibiotic therapy that ranged from four to fifty-two weeks.

65 male and 60 female patients ranging in age from 2 to 149 months were enrolled as outpatients in the trial and were available for post-surgical study and analysis. The median age of all the children in the trial was 37.0 months. 61 had recurrent acute otitis media, 51 had persistent otitis media with effusion and 13 had both acute otitis media and persistent otitis media with effusion. 75 of the right ears and 76 of the left ears were noted to show retraction. 7 of the right ears and 7 of the left ears were noted to have severe retraction.

The anti-microbial tympanostomy tubes used in the trial were manufactured of silicone elastomer impregnated with 6.5±1.5 weight % silver oxide. The impregnated silver oxide gave the tubes a dense black appearance that could easily be contrasted with commercially available colored tubes. Therefore, a set of control tubes was dyed black with a non-bacteriostatic and biocompatible pigment to match the experimental devices. The control tubes were designated "A" and the anti-microbial tubes were designated "B" and labeled by the manufacturer.

The tubes were grossly indistinguishable and neither the principal investigator nor the co-investigators knew which tube represented the control and which represented the anti-microbial tympanostomy tube. Each patient received an anti-microbial tympanostomy tube in one ear and a control tube in the contralateral ear. The assignment of tubes was done on a random basis.

At the time of surgery numerically coded surgical forms were removed by the investigator from a sealed consecutive numbered envelope to insure randomization of tube placement. The code was revealed to the principal investigator after completion of the study and condensation of the data. The surgical data form contained the tube assignment: "A"-right, "B"-left, or "A"-left, "B"-right.

The 125 patients underwent surgery for implantation of the anti-microbial and standard tympanostomy tubes bilaterally. Randomized assignment of tympanostomy tubes to right or left ears achieved a reasonable balance. 61 patients had the "A" tube in the right ear and the "B" tube in the left ear and 64 patients had the "A" tube in the left ear and "B" tube in the right ear. No remarkable patient events or characteristics were noted upon enrollment into the trial.

The surgical procedure was standardized at each site to the extent possible between investigators and from patient to patient. Operations were performed under general anesthesia and standard surgical and operating practices were observed. Surgical preparation was not performed to the ear canal.

A small radial incision was made in the anterior-inferior portion of the tympanic membrane, and any fluid present was aspirated. The fluid type was noted and the location of the incision documented on the entry form. The anti-microbial tympanostomy and control tubes were inserted through the myringotomy in a standard fashion to allow the inner flange to contact the inner surface of the tympanic membrane. Any bleeding during surgery was controlled with topical 1% xylocaine with 1:100,000 epinephrine. Antibiotic drops were not instilled into the middle ear following the implantation.

Following surgery, each patient was scheduled for follow-up evaluations according to the following schedule:

1 week
1 month
3 months
6 months
9 months
1 year
Additional follow-up as necessary if tube was not extruded.

At each follow-up visit the patient underwent otoscopic examination. Cultures were taken as appropriate and atorrhea, if present, was treated with conventional antibiotic therapy.

Statistical Tests

Data management was performed using Lotus 1-2-3 for Windows. Statistical testing was accomplished using NCSS Version 5.0. Incidence or rates of otorrhea, blockage, extrusion and complications following surgical implant of experimental and control tympanostomy tubes were correlated by reason of implantation in alternate ears in the same patient.

Fisher's 2×2 exact test was used to compare non-parametric data. Student's T-test for independent variables was used to compare parametric data.

The criteria for statistical significance was at the α=0.05 level.

Surgical Findings

The findings of the contents of the middle ear were roughly equivalent in the right and left ears, and are noted in Table 5, which follows:

TABLE 5

Middle Ear Contents at the Time of the Surgery

| Middle Ear Content | A | B |
|---|---|---|
| None | 40 | 45 |
| Serous | 31 | 24 |
| Mucoid | 42 | 46 |
| Purulent | 8 | 7 |
| Other | 4 | 3 |

At the time of surgery, retraction of the tympanic membrane was noted in 36 "A" implanted ears (one instance with severe retraction) and in 36 "B" implanted (3 with severe retraction.) No instances of tympanosclerosis or other pathology was noted. There were no cholesteatomas.

Post-Operative Findings

During the post-operative period implanted ears were evaluated at intervals for complications and otorrhea. The children's parents were questioned about a history of otorrhea in the interim period between the previous visit and the current visit. There were a total of four hundred seventy-nine post-operative encounters per patient. Post-operative encounters were not recorded after the tubes had extruded and some patients failed to complete all scheduled post-operative visits.

Granulation tissue formation around the tympanostomy tubes was noted during four patient encounters: two instances following implantation of the "A" tube, and two instances following implantation of the "B" tube (p=n.s.). Extrusion of tympanostomy tubes occurred as expected with typical Donaldson design tympanostomy tube. The time to extrusion was known in 75 instances with implantation with the "A" tube and 82 instances of implantation with the "B" tube. The average time to extrusion was 27.0 weeks±13.0 weeks for the "A" tube and 25.1±14.8 for the "B" tube (p=n.s.). 8.46% of "A" tubes and 12.31% of "B" tubes were known to have extruded within 90 days of implantation.

No instances of cholesteatoma were noted.

There was a statistically significant difference in the incidence of otorrhea on patient encounter between "A" (control) "B" (anti-microbial) tubes ("A"-36/368 [9.78%] and "B"-19/374 [5.08%]) (p=0.010) (Fisher's exact test for 2×2 tables). When the outcome variable was considered to be either otorrhea at the time of the post-operative encounter or a history of otorrhea prior to that encounter, the criteria was met in 59/368 [16.03%] of those implanted with the "A" tubes and 28/374 [7.49%] of those implanted with the "B" tubes (p=0.0002) (Fisher's exact test for 2×2 tables.)

Considering the rationale that postoperative otorrhea during the first week may have been a result of infection within the middle ear fluid and not secondary infection, otorrhea rates were analyzed excluding the first week. When the instance of otorrhea on patient encounters excluding the first post-operative week was evaluated, the incidence of otorrhea in the ears implanted with the "A" tube was 27/255 [10.59%] and 10/261 [3.83%] with the ears implanted with the "B" tube. (p=0.002).

There was no difference in the incidence of otorrhea during the first week after surgical implantation of the tubes.

However, the data indicated a significant decrease in the incidence of otorrhea encountered on post-operative visits overall (p=0.010), and a significant decrease in the incidence of otorrhea was observed during post-operative encounters after the first week of implantation (p=0.002).

What is claimed is:

1. A method of making a tympanostomy tube that is biologically compatible with the otologic tissue of the middle ear and that exhibits antimicrobial activity sufficient to alleviate the incidence of otorrhea following surgery, said method comprising the steps of mixing a microporous, gas permeable silicone gum resin in the form of a paste with a silver compound in the form of particles;

milling the mixture to uniformly disperse the silver compound particles throughout the silicone paste;

forming the milled product into a tympanostomy tube;

post curing the tympanostomy tube; and obtaining an antimicrobial effect with the tympanostomy tube by migration of the silver compound to the surface of the tube via pores in the resin.

2. A method as recited in claim 1 wherein said mixing step includes mixing a silicone gum resin in the form of a paste with a concentration of about 0.5 to about 15% by weight of a silver compound in the form of particles having an average size ranging from about 5 to about 100 microns.

3. A method as recited in claim 1 wherein said forming step is performed by transfer molding.

4. A method as recited in claim 1 wherein said forming step is performed by casting.

5. A method as recited in claim 1 wherein said forming step is performed by extrusion.

6. A method as recited in claim 1 wherein said post curing step is performed at a temperature of about 120° centigrade for a period of about 1.5 hours.

7. A method of making a tympanostomy tube that is biologically compatible with the otologic tissue of the middle ear and that exhibits antimicrobial activity sufficient to alleviate the incidence of otorrhea following surgery, said method comprising the steps of mixing a microporous, gas permeable elastomeric resin with a silver compound in the form of particles;

uniformly dispersing the silver compound particles throughout the resin;

forming the resin with the uniformly dispersed particles therein into a tympanostomy tube;

post curing the tympanostomy tube; and obtaining an antimicrobial effect with the tympanostomy tube by migration of the silver compound to the surface of the tube via pores in the resin.

8. A method as recited in claim 7 wherein said mixing step includes mixing a silicone gum resin in the form of a paste with the silver compound in the form of particles.

9. A method as recited in claim 8 wherein said mixing step includes mixing the silicone gum resin in the form of a paste with a concentration of about 0.5 to about 15% by weight of the silver compound in the form of particles having an average size ranging from about 5 to about 100 microns.

10. A method as recited in claim 8 wherein said step of uniformly dispersing includes milling the mixture of silicone gum resin and silver compound.

11. A method as recited in claim 7 wherein said forming step is performed by transfer molding.

12. A method as recited in claim 7 wherein said forming step is performed by casting.

13. A method as recited in claim 7 wherein said forming step is performed by extrusion.

14. A method as recited in claim 7 wherein said post curing step is performed at a temperature of about 120° centigrade for a period of about 1.5 hours.

15. A method as recited in claim 14 wherein said post curing step is performed by baking.

16. A method of making a tympanostomy tube that is biologically compatible with the otologic tissue of the middle ear and that exhibits antimicrobial activity sufficient to alleviate the incidence of otorrhea following surgery, said method comprising the steps of mixing a microporous, gas-permeable elastomeric resin with a silver compound in the form of particles;

uniformly dispersing the silver compound particles throughout the resin;

forming the resin with the uniformly dispersed particles therein into a tympanostomy tube;

post curing the tympanostomy tube; and obtaining an antimicrobial effect with the tympanostomy tube by leaching antimicrobial silver ions from the tube.

17. A method as recited in claim 16 wherein said mixing step includes mixing a silicone gum resin in the form of a paste with the silver compound in the form of particles.

18. A method as recited in claim 17 wherein said mixing step includes mixing the silicone gum resin in the form of a paste with a concentration of about 0.5 to about 15% by weight of the silver compound in the form of particles having an average size ranging from about 5 to about 100 microns.

19. A method as recited in claim 17 wherein said step of uniformly dispersing includes milling the mixture of silicone gum resin and silver compound.

20. A method as recited in claim 16 wherein said post curing step is performed by baking at a temperature of about 120° centigrade for a period of about 1.5 hours.

* * * * *